United States Patent [19]

Takasuka et al.

[11] 4,075,498
[45] Feb. 21, 1978

[54] NON-WOVEN FABRIC DEFECT DETECTING DEVICE

[75] Inventors: Kaoru Takasuka; Masatatsu Takahashi; Sadaji Nishimura, all of Fuji, Japan

[73] Assignee: Asahi Kasei Kogyo Kabushiki Kaisha, Osaka, Japan

[21] Appl. No.: 670,610

[22] Filed: Mar. 26, 1976

[30] Foreign Application Priority Data

Mar. 31, 1975 Japan ............................ 50-38672

[51] Int. Cl.² ............................................ G01N 21/32
[52] U.S. Cl. ..................................... 250/562; 250/572; 356/238
[58] Field of Search ............... 250/563, 205, 562, 571, 250/572, 559; 356/237, 238, 199, 200; 235/92 V; 178/DIG. 3

[56] References Cited

U.S. PATENT DOCUMENTS

| 3,534,402 | 10/1970 | Crowell et al. | 250/571 |
| 3,588,513 | 6/1971 | Takatsuki et al. | 250/562 |
| 3,729,619 | 4/1973 | Laycak et al. | 235/92 V |
| 3,866,054 | 2/1975 | Wolf | 250/562 |
| 3,898,469 | 8/1975 | Nichols et al. | 250/563 |

FOREIGN PATENT DOCUMENTS 2,322,803  11/1973  Germany ............................ 356/237

Primary Examiner—Alfred E. Smith
Assistant Examiner—David K. Moore
Attorney, Agent, or Firm—Sughrue, Rothwell, Mion, Zinn and Macpeak

[57] ABSTRACT

Disclosed is a non-woven fabric defect detecting device in which light is applied to a travelling non-woven fabric to optically or electrically scan the non-woven fabric in its widthwise direction and the light from each point on the non-woven fabric is converted into an electric signal. The converted electric signal is classified into a plurality of levels to detect at least a hole and a heavy filling bar. The durations of these detected outputs are counted in the form of clocks and grading of the quality of the non-woven value is achieved based on the count values. The abovesaid converted output is differentiated and the differentiated output above a predetermined level is detected as fold bar.

8 Claims, 28 Drawing Figures

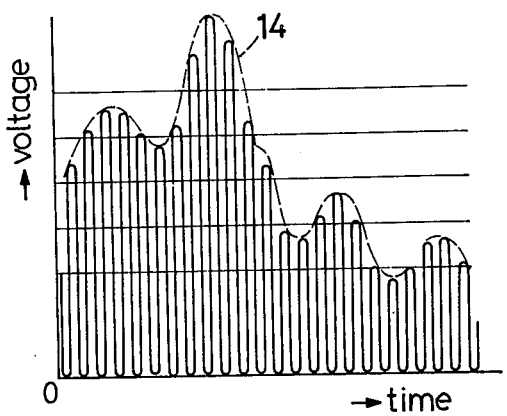
FIG. 3A
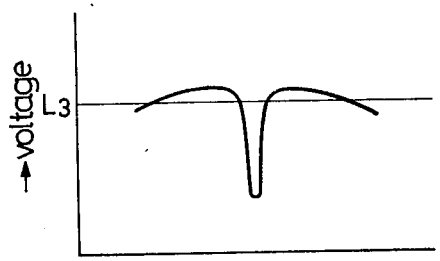
FIG. 3D
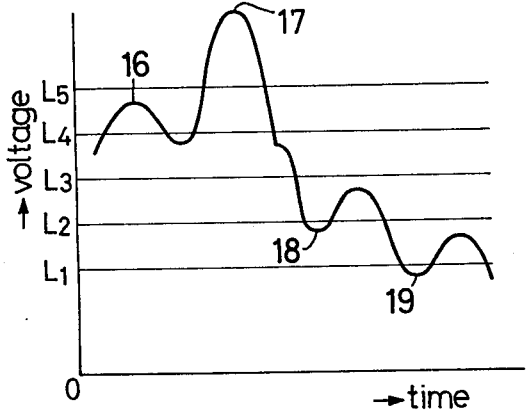
FIG. 3B
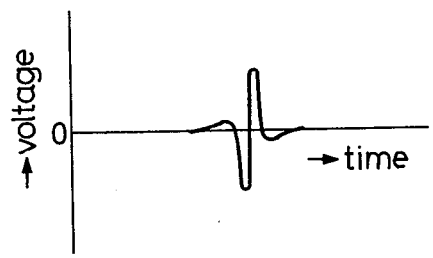
FIG. 3E
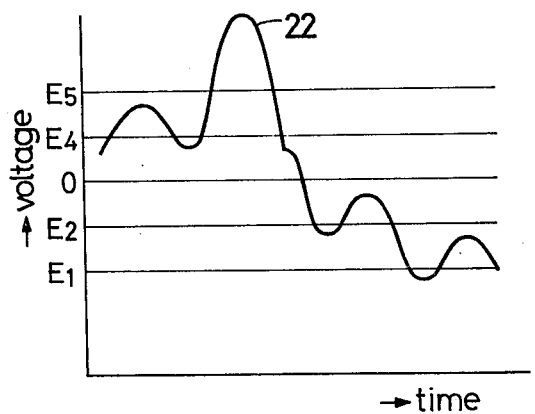
FIG. 3C
FIG. 5

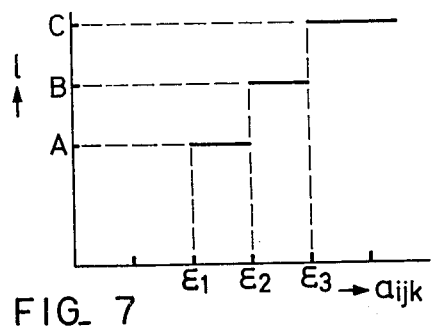
FIG. 7
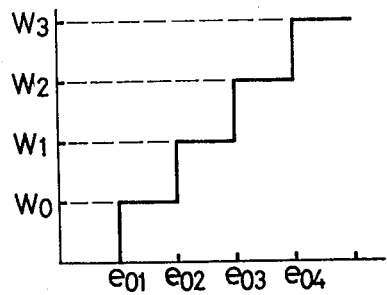
FIG. 9A
FIG. 8
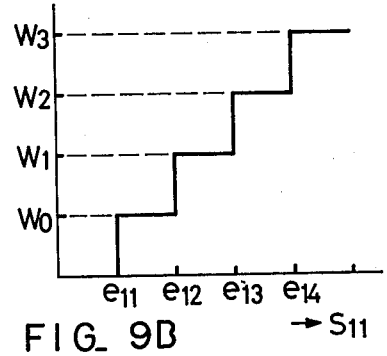
FIG. 9B
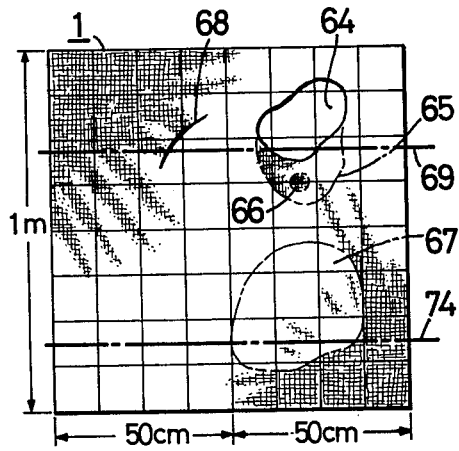
FIG. 10
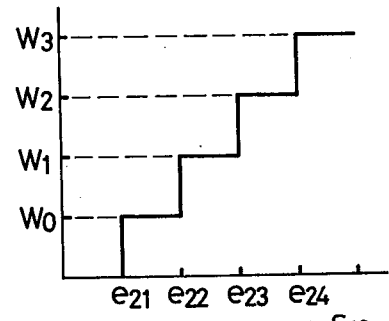
FIG. 9C
FIG. 11A
FIG. 11B
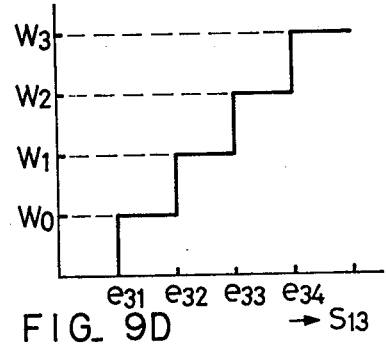
FIG. 9D

FIG. 12A

| 0 | 0 | 0 | 0 | 0 | 485 | 23 | 0 |
|---|---|---|---|---|---|---|---|
| 0 | 0 | 0 | 0 | 0 | 361 | 355 | 0 |
| 0 | 0 | 0 | 0 | 1731 | 8661 | 6951 | 2 |
| 0 | 0 | 0 | 0 | 0 | 0 | 0 | 0 |
| 0 | 0 | 0 | 0 | 0 | 0 | 0 | 0 |
| 0 | 0 | 0 | 0 | 0 | 0 | 0 | 0 |
| 0 | 0 | 0 | 0 | 0 | 0 | 0 | 0 |
| 0 | 0 | 0 | 0 | 0 | 0 | 0 | 0 |

FIG. 12D

| 0 | 0 | 0 | 0 | 0 | 0 | 0 | 0 |
|---|---|---|---|---|---|---|---|
| 0 | 0 | 0 | 0 | 0 | 0 | 0 | 0 |
| 0 | 0 | 0 | 0 | 0 | 0 | 0 | 0 |
| 0 | 0 | 0 | 0 | 0 | 0 | 0 | 0 |
| 0 | 0 | 0 | 0 | 0 | 0 | 0 | 0 |
| 0 | 0 | 0 | 0 | 0 | 0 | 0 | 0 |
| 0 | 0 | 0 | 0 | 0 | 0 | 0 | 0 |
| 0 | 0 | 0 | 0 | 0 | 0 | 0 | 0 |

FIG. 12B

| 1853 | 1426 | 1274 | 10 | 9792 | 12231 | 12682 | 2405 |
|---|---|---|---|---|---|---|---|
| 777 | 343 | 229 | 28 | 11160 | 9922 | 11202 | 2956 |
| 803 | 30 | 810 | 127 | 12792 | 9537 | 11255 | 7995 |
| 1275 | 195 | 1497 | 1642 | 11842 | 9786 | 990 | 4989 |
| 2773 | 1360 | 414 | 429 | 12363 | 13345 | 10904 | 3730 |
| 1816 | 428 | 708 | 2 | 13415 | 11322 | 13452 | 6026 |
| 1496 | 786 | 1031 | 345 | 12642 | 11774 | 11155 | 5203 |
| 2058 | 299 | 509 | 109 | 12077 | 14202 | 11988 | 5224 |

FIG. 12C

| 1 | 1 | 20 | 18 | 0 | 0 | 29 | 52 |
|---|---|---|---|---|---|---|---|
| 2 | 8 | 4 | 43 | 0 | 0 | 27 | 1 |
| 0 | 0 | 0 | 23 | 0 | 835 | 286 | 1 |
| 1 | 0 | 0 | 333 | 0 | 23 | 141 | 0 |
| 0 | 0 | 0 | 13 | 0 | 0 | 0 | 0 |
| 0 | 0 | 0 | 73 | 0 | 0 | 0 | 0 |
| 0 | 0 | 0 | 5 | 0 | 0 | 0 | 0 |
| 0 | 3 | 1 | 0 | 0 | 0 | 0 | 0 |

FIG. 12E

| 0 | 4 | 0 | 0 | 0 | 4 | 9 | 0 |
|---|---|---|---|---|---|---|---|
| 1 | 0 | 1 | 11 | 7 | 4 | 18 | 7 |
| 0 | 1 | 11 | 4 | 15 | 24 | 15 | 27 |
| 0 | 0 | 0 | 1 | 6 | 12 | 3 | 2 |
| 1 | 1 | 0 | 2 | 0 | 0 | 0 | 0 |
| 0 | 0 | 0 | 0 | 0 | 7 | 0 | 0 |
| 0 | 0 | 0 | 0 | 0 | 0 | 0 | 0 |
| 0 | 0 | 0 | 0 | 0 | 0 | 0 | 0 |

|  | $\varepsilon_1$ | $\varepsilon_2$ | $\varepsilon_3$ |
|---|---|---|---|
| $D_1$ | 2 | 60 | 500 |
| $D_2$ | 5000 | 15000 | 30000 |
| $D_3$ | 5000 | 15000 | 30000 |
| $D_4$ | 2 | 150 | 1000 |
| $D_5$ | 10 | 32 | 64 |

FIG. 13

|  | A | | | | B | | | | C | | | |
|---|---|---|---|---|---|---|---|---|---|---|---|---|
|  | $e_{11}$ | $e_{12}$ | $e_{13}$ | $e_{14}$ | $e_{21}$ | $e_{22}$ | $e_{23}$ | $e_{24}$ | $e_{31}$ | $e_{32}$ | $e_{33}$ | $e_{34}$ |
| $D_1$ | 0 | 1 | 31 | 32 | 0 | 0 | 1 | 32 | 0 | 0 | 0 | 1 |
| $D_2$ | 1 | 6 | 21 | 32 | 0 | 3 | 14 | 32 | 0 | 3 | 14 | 32 |
| $D_3$ | 1 | 6 | 21 | 32 | 0 | 3 | 14 | 32 | 0 | 3 | 14 | 32 |
| $D_4$ | 1 | 6 | 32 | 32 | 0 | 1 | 20 | 32 | 0 | 0 | 1 | 2 |
| $D_5$ | 1 | 11 | 26 | 32 | 0 | 1 | 26 | 32 | 0 | 13 | 26 | 32 |

FIG. 14

| $D_1$ | normal |
|---|---|
| $D_2$ | normal |
| $D_3$ | normal |
| $D_4$ | normal |
| $D_5$ | $W_0$ |

FIG. 15A

| $D_1$ | $W_3$ |
|---|---|
| $D_2$ | $W_2$ |
| $D_3$ | normal |
| $D_4$ | $W_0$ |
| $D_5$ | $W_1$ |

FIG. 15B though the inspection is effected by visual inspection of the non-woven fabric and the amount of skill and is subject to each inspector's individual difference in judgement as to the defects. That is, decision of

NON-WOVEN FABRIC DEFECT DETECTING DEVICE

BACKGROUND OF THE INVENTION

This invention relates to a device for detecting defects of the so-called non-woven fabric manufactured in the form of cloth without weaving.

In the prior art, for the grading of the quality of a non-woven fabric, the non-woven fabric once wound in the form of a roll is unwound and passed over an inspection table of frosted glass and, in this case, light of a fluorescent lamp is applied to the underside of the frosted glass to facilitate finding of defects of the non-woven fabric and an inspector judges the defects by visual inspection and counts the defects of respective kinds with counters by manual operation. That is, the defect of the non-woven fabric is classified into a hole having a diameter more than 2 mm, a fold bar which is folding or overlapping of a certain area of the non-woven fabric, a heavy filling bar that a certain area of the non-woven fabric is remarkedly thick as compared with the neighboring area and a weight bar that the non-woven fabric is a little thick or thin over a wide area. These four defects are found out by visual inspection of the non-woven fabric passing over the aforementioned frosted glass and counted by counters respectively corresponding to the four kinds of defects. The detection of the defects of the non-woven fabric in the prior art is achieved by such visual inspection and subject to individual inspectors' judgement and not so objective. Further, since the non-woven fabric is travelling the inspection requires a considerable amount of skill and is subject to each inspectors' individual difference in judgement as to the defects. That is, decision of the defects is likely to vary greatly according to the particular inspector, so that the inspection is subjective and inaccurate. Moreover, such visual inspection is very laborious. In addition, it is impossible to detect the defects by such a conventional method in the course of the fabrication of the non-woven fabric, so that it is necessary for visual inspection to spread the non-woven fabric once rolled after manufactured. Thus, with such conventional method of inspection, it is impossible to effect grading of the quality of non-woven fabrics during their manufacture for classifying them according to the quality or for obtaining non-woven fabrics of the same quality by controlling the manufacturing process.

The object of this invention is to provide a non-woven fabric defect detecting device which is capable of automatic, subjective and accurate detection of various defects of a non-woven fabric in the course of its manufacture and enables grading of the quality of the fabric, if necessary.

SUMMARY OF THE INVENTION

In accordance with this invention, light is applied to a travelling non-woven fabric and transmitted lights or reflected lights at respective points on the non-woven fabric are converted into electric signals. The non-woven fabric is scanned so that the converted outputs may be picked up one after another in the widthwise direction of the non-woven fabric. The electric signals are each classified into a plurality of levels and detected for each kind of defect. That is, a portion of the converted electric signal above a predetermined level is judged as a hole or an extremely thick area or a portion that a little higher level continues is detected as a weight bar which is thick or thin over a relatively wide area. Further, the electric signal is differentiated and the differentiated output having a peak value higher than a certain level is detected as a fold bar. The fold bar is thus detected in the form of a differentiated pulse, so that the differentiated values of the portions of the electric signal corresponding to the edges of the hole are also detected as fold bars. The hole is the worst defect of the non-woven fabric but, unlike such a defect, the fold bar is detected because it is not favorable when its number is large. Accordingly, for example, in the grading of quality of the non-woven fabric, the fabric is immediately rejected even when one hole is found but, as for the fold bar, the non-woven fabric is rejected when ten fold bars are found. Therefore, the abovesaid hole and the edge of the heavy filling bar are both detected as fold bars but this error is not so serious and considerably accurate quality evaluation can be effected.

Further, the heavy filling bar and the hole are respectively counted as the heavy weight and the light weight and, since these defects are extremely bad defects as compared with the heavy weight and the light weight, that is, weight bars, their addition to the weight bars does not present any problem.

The hole, the heavy filling bar, the heavy weight and the light weight are respectively detected by the comparison of the converted electric signals with reference levels and these reference levels are set different from one another according to the kinds of defects. The gains of amplifiers for amplifying the converted electric signals to be applied to comparator-detector circuits for detecting small bars, that is, the heavy weight and the light weight, are selected larger than the gains of amplifiers for amplifying the converted electric signals to be applied to comparator circuits for detecting large bars, that is, the hole and the heavy filling bar, by which the detection of the small bars by comparison can be achieved with accuracy. The average level of the converted electric signal is detected and the average level of the electric signal applied to defect detecting means is controlled to remain constant in accordance with the detected average level. To perform this, for example, the quantity of light from the light source is controlled in accordance with the abovesaid detected electric signal level, by which the photoelectric conversion gain is controlled or the gain of the amplifier for amplifying the converted signal is controlled.

The duration of each of the defects detected by comparison is counted, for example, in the form of clock pulses. The fold bars detected by differentiation are also counted. The count values of the respective defects are obtained for each unit area of the non-woven fabric. The count values are each classified into a plurality of ranks and, in an evaluation area which is an assembly of the unit areas, the numbers of the rank of each kind of defect are individually added together and, based on the results of the additions, the grading of quality of the non-woven fabric is effected. For such processing, an electronic computer can be employed.

BRIEF DESCRIPTION OF THE DRAWINGS

FIGS. 3A to 3E are waveform diagrams explanatory of the operation of the device of this invention;

FIG. 5 is a diagram showing the relationship between an evaluation area and unit areas of a non-woven fabric;

FIG. 7 is a graph showing the relationship between the number of defects and ranks;

FIG. 8 is a table showing the ranks of defects and the total values of the defects of each rank;

FIGS. 9A to 9D are graphs respectively showing classification based on the total values and set values of each rank;

FIG. 10 is a diagram showing a non-woven fabric employed in an experiment of this invention;

FIGS. 11A and 11B are graphs, each showing one example of the output from an envelope detector circuit;

FIGS. 12A to 12E are tables respectively showing the count values of the individual defects in each unit area;

FIG. 13 is a table showing the relationship between threshold values for ranking and the defects;

FIG. 14 is a table showing the relationship between the respective defects and the set value for classification; and FIGS. 15A and 15B are tables showing the results of classification of the respective defects.

DESCRIPTION OF THE PREFERRED EMBODIMENT

Figure 1:
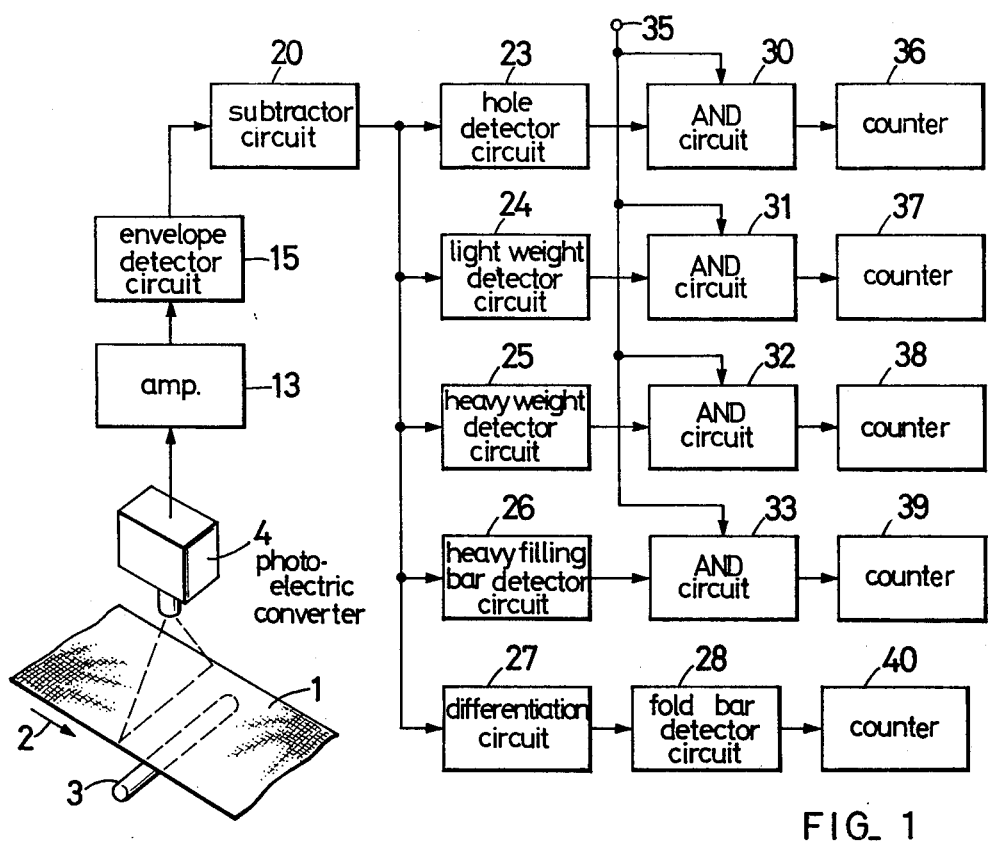
FIG. 1 is a block diagram illustrating one embodiment of this invention.

In FIG. 1, reference numeral 1 indicates a non-woven fabric, which is driven in a certain direction 2. A light source 3 is disposed, for example, below the non-woven fabric 1 for irradiating it by a uniform light in its widthwise direction and a photoelectric converter 4 is disposed, for example, above the non-woven fabric 1. The photoelectric converter 4 is positioned in opposing relationship to the light source 3 so that images at respective points of the non-woven fabric 1 in its widthwise direction may be thrown on the conversion surface of the photoelectric converter 4. The conversion surface has incorporated therein an array of photodiodes, which charge in their individual capacitors the electrical outputs respectively corresponding to transmitted lights at the respective points of the non-woven fabric 1. The capacitors are sequentially changed over by a switching circuit formed with a MOS transistor to discharge the charges of the capacitors one after another. That is, the non-woven fabric 1 is equivalently scanned in its widthwise direction and the transmitted lights at its respective points are sequentially converted into electric signals and, in addition, the scanning position is shifted by the travel of the non-woven fabric 1 in its lengthwise direction and the transmitted lights at the respective points on the entire area of the non-woven fabric 1 are obtained in the form of electric signals one after another. The photoelectric converter 4 may be such, for example, as one that is manufactured and sold by Reticon Inc. of U.S.A., commercially known under the name of Solid State Line Scanner.

Figure 2:
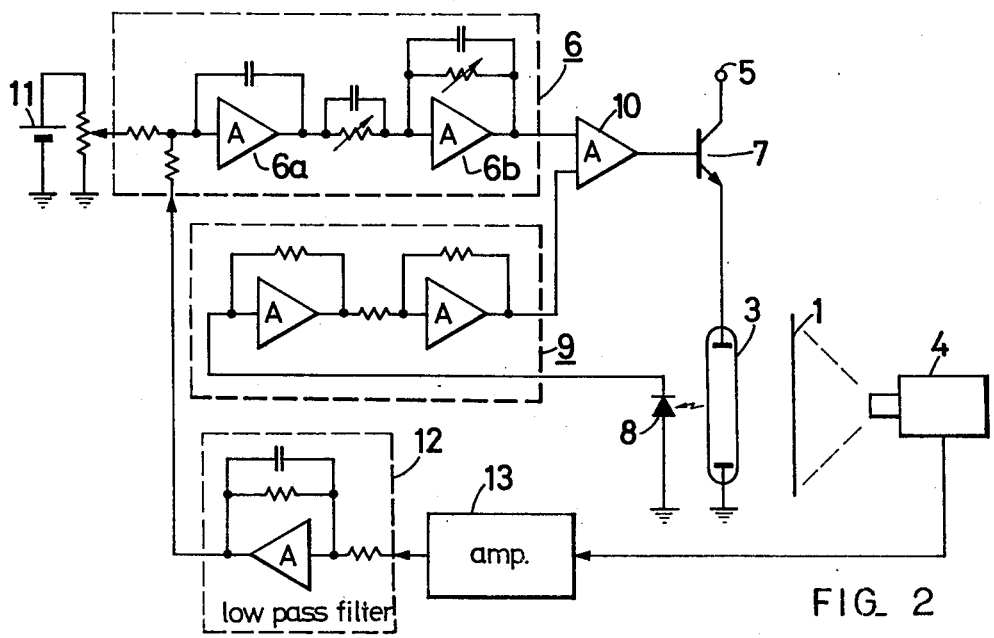
FIG. 2 is a block diagram showing one example of output level stabilizing means employed in FIG. 1.

In order that the quantity of light of the light source 3 may be maintained at a constant value at all times, the light source 3 used is, for example, a DC-lit fluorescent lamp as shown in FIG. 2 which extends in the widthwise direction of the non-woven fabric 1 and is connected at one end to a power source terminal 5 and grounded at the other end. Between the power source terminal 5 and the fluorescent lamp 3, there is connected a control transistor 7 in the emitter-collector fashion. The light emitted from the fluorescent lamp 3 is converted into an electric signal by means of a light receiving element 8 such as a solar battery and its output is amplified by an amplifier 9 and then applied to one input terminal of a comparator-amplifier 10. To the other input terminal of the comparator-amplifier 10, a reference voltage is supplied from a circuit 6 and, by the output from the comparator-amplifier 10, the base of the transistor 7 is controlled. Namely, an increase in the quantity of light from the fluorescent lamp 3 causes a decrease in the base voltage of the transistor 7 to limit the discharge current of the fluorescent lamp 3. Conversely, when the quantity of light from the fluorescent lamp 3 decreases, the transistor 7 operates to increase the discharge current of the fluorescent lamp 3. Thus, the quantity of light from the fluorescent lamp 3 is always held at a constant value. Further, the mean value of the output from the photoelectric converter 4 is maintained constant. That is, the output from the converter 4 is applied to an ultra-low-pass filter 12, if necessary, after being amplified by an amplifier 13, and then supplied to the circuit 6, in which the difference between the output from the filter 12 and a set voltage of the power source 11 is obtained. A proportional plus integral output of the deviation voltage is derived from a circuit 6a and applied as a reference voltage to the comparator-amplifier 10 through a stabilizing circuit 6b employed in an ordinary feedback control system. In this manner, the average of the output from the photoelectric converter 4 is held constant.

Turning back to FIG. 1, the output from the photoelectric converter 4 is amplified by a buffer amplifier 13. The amplified output contains a pulse having a peak value corresponding to the amount of charges produced by every switching of the respective capacitors in the photoelectric converter 4 and the overall envelope 14 of the amplified output varies with the quantity of transmitted light at the scanning position in the widthwise direction of the non-woven fabric 1, as illustrated in FIG. 3A. The output from the buffer amplifier 13 is applied to a circuit 15 to detect an envelope signal corresponding to the envelope 14. The circuit 15 may be the so-called sample holding circuit, which is manufactured by Hybrid System Inc. of U.S.A. and placed on the market under the commercial name of Semiconductor Integrated Circuit SH730. The output from the circuit 15 becomes such as depicted in FIG. 3B. In FIG. 3B, reference character $L_3$ indicates a level at which the non-woven fabric 1 has no levelling or bars; $L_2$ and $L_1$ designate two levels lower than the level $L_3$; and $L_4$ and $L_5$ denote two levels higher than the level $L_3$. Reference numerals 16 to 19 respectively identify some particular portions of the non-woven fabric 1. The portion 16 having a level higher than the level $L_4$ indicates the so-called light weight that the quantity of light transmitted through the non-woven fabric 1 at this portion is relatively large and that the non-woven fabric 1 is thin over a relatively wide area. Further, the portion 17 having a level higher than the level $L_5$ indicates that the quantity of light transmitted through this portion is remarkably large and that a large hole of more than 2 mm, for example, is formed in the non-woven fabric 1. On the other hand, the portion 18 having a level lower than the level $L_2$ indicates the so-called heavy weight that this portion is thick as a whole and the portion 19 having a level lower than the level $L_1$ indicates that this portion is particularly thick as compared with the neighboring area.

The entire length of each of the portions lower than the levels $L_1$ and $L_2$ and the portions higher than the levels $L_4$ and $L_5$ are detected in a digital fashion. To this end, the envelope signal derived from the circuit 15 is subtracted by the level $L_3$ in a subtractor circuit 20 and converted into such a signal 22 as shown in FIG. 3C in which the level $L_3$ corresponds to a level 0 and the levels $L_1$, $L_2$, $L_4$ and $L_5$ respectively correspond to levels $-E_1$, $-E_2$, $E_2$ and $E_5$. The portion of the signal 22 higher than the level $E_5$ is detected by a hole detector circuit 23; the portion higher than the level $E_4$ is detected by a light weight detector circuit 24; the portion lower than the level $-E_2$ is detected by a heavy weight detector circuit 25; and the portion lower than the level $-E_1$ is detected by a heavy filling bar detector circuit 26. Further, the signal 22 is differentiated by a differentation circuit 27 and that portion of the differentiated output which is higher than a predetermined level, is detected by a fold bar detector circuit 28. The period of time during which the detected outputs are derived from these detector circuits, is counted in the form of pulses. That is, the outputs from the circuits 23 to 26 are respectively AND'ed by AND circuits 30 to 33 with clocks applied thereto from a terminal 35. The outputs from these AND circuits 30 to 33 are respectively counted by counters 36 to 39. The output from the detector circuit 28 is counted by a counter 40.

Figure 4:
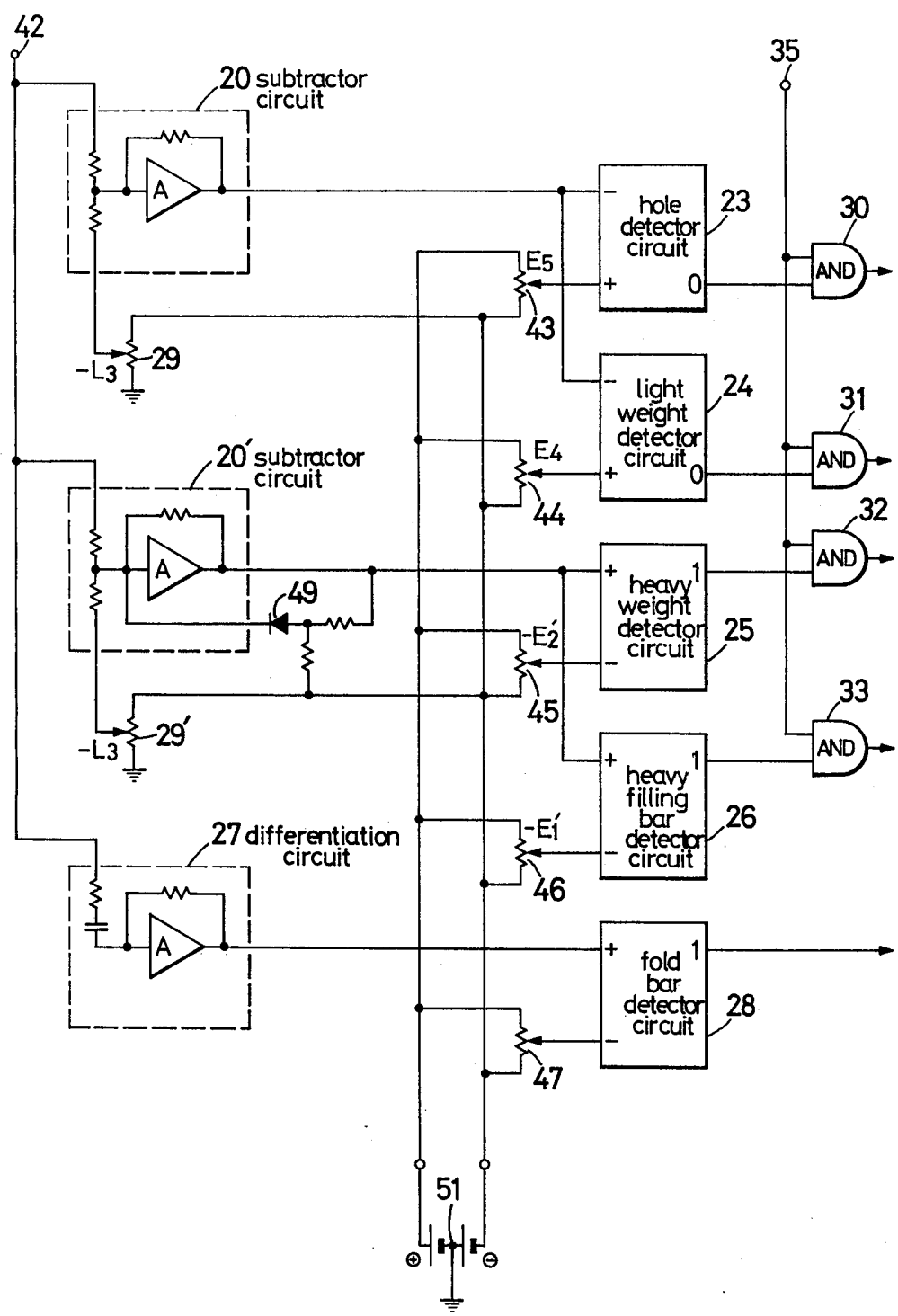
FIG. 4 is a block diagram showing a modified form of the device of this invention.

FIG. 4 shows a modified form of the embodiment of FIG. 1. From an input terminal 42, the envelope signal 22 derived from the circuit 15 in FIG. 1 is applied. In an adder circuit 20, a voltage $-L_3$ from a variable resistor 29 is added to the abovesaid envelope signal 22 and, in the hole detector circuit 23, the output from the adder circuit 20 is compared with a voltage $+E_5$ from a variable resistor 43 and the portion exceeding the voltage $+E_5$ is applied as a positive constant level to the AND circuit 30. Further, the envelope signal 22 from the input terminal 22 is added with a voltage from a variable resistor 29' in the adder circuit 20' and, at the same time, amplified. And the positive, large amplitude portion of the amplified signal is amplitude limited by a diode 49 and its relatively low level, that is, the level of the portion lower than the voltages $-E_2$ and $-E_1$, is raised to facilitate the detection thereof. In this case, it is also possible, if necessary, to design that a large value is subtracted in a direction further negative than the level $-L_3$ to render the level corresponding to the voltage $-E_2$ positive-going. The output from the adder circuit 20' is compared with voltages $-E_2'$ and $-E_1'$ respectively corresponding to these $-E_2$ and $-E_1$ from variable resistors 45 and 46 in the heavy weight detector circuit 25 and the heavy filling bar detector circuit 26, respectively. The portion lower than these levels produces outputs of constant levels from the respective detector circuits and these outputs are respectively applied to the AND circuits 32 and 33. Further, the envelope signal 22 from the input terminal 42 is differentiated by the analog differentiation circuit 27 usually employed and the differentiated output is compared by the fold bar detector circuit 23 with the output from a variable resistor 47 which is a negative reference voltage and the portion lower than the negative reference voltage is provided as a positive output of a constant level. Both ends of each of the resistors 29, 29' and 43 to 47 are connected to both ends of a power source 51.

Thus, clock pulses are produced respectively corresponding to the hole portion 17, the light weight portion 16, the heavy weight portion 18 and the heavy filling bar portion 19, and counted by the counters individually corresponding thereto. Accordingly, the numbers of such hole portions 17 and such light weight portions are respectively detected by the count values of the counters 36 and 37. In a similar manner, the numbers of the other bars are detected. The fold bar results from folding of some fibers unusually pulled by some cause and forms a streak that the folded portion is thick and that the margin of the thick portion is thin. Accordingly, the output of the envelope signal 22 corresponding to the fold bar has such a waveform as shown in FIG. 3D in which the output rapidly lowers with respect to the reference level $L_3$ just like a pulse but the preceding and following portions are a little higher than the level $_3$. This output is differentiated by the differentiation circuit 27 to provide such an output as depicted in FIG. 3D. That is, in the case of the fold bar, a pair of upper and lower pulses adjacent to each other are produced as shown. The fold bar looks like a streak and, in this case, the thickness of the non-woven fabric abruptly changes. In such a case where the peak value of the differentiated pulse becomes lower than a certain level, it is detected as the fold bar and its number is counted by a counter 40.

Figure 6:
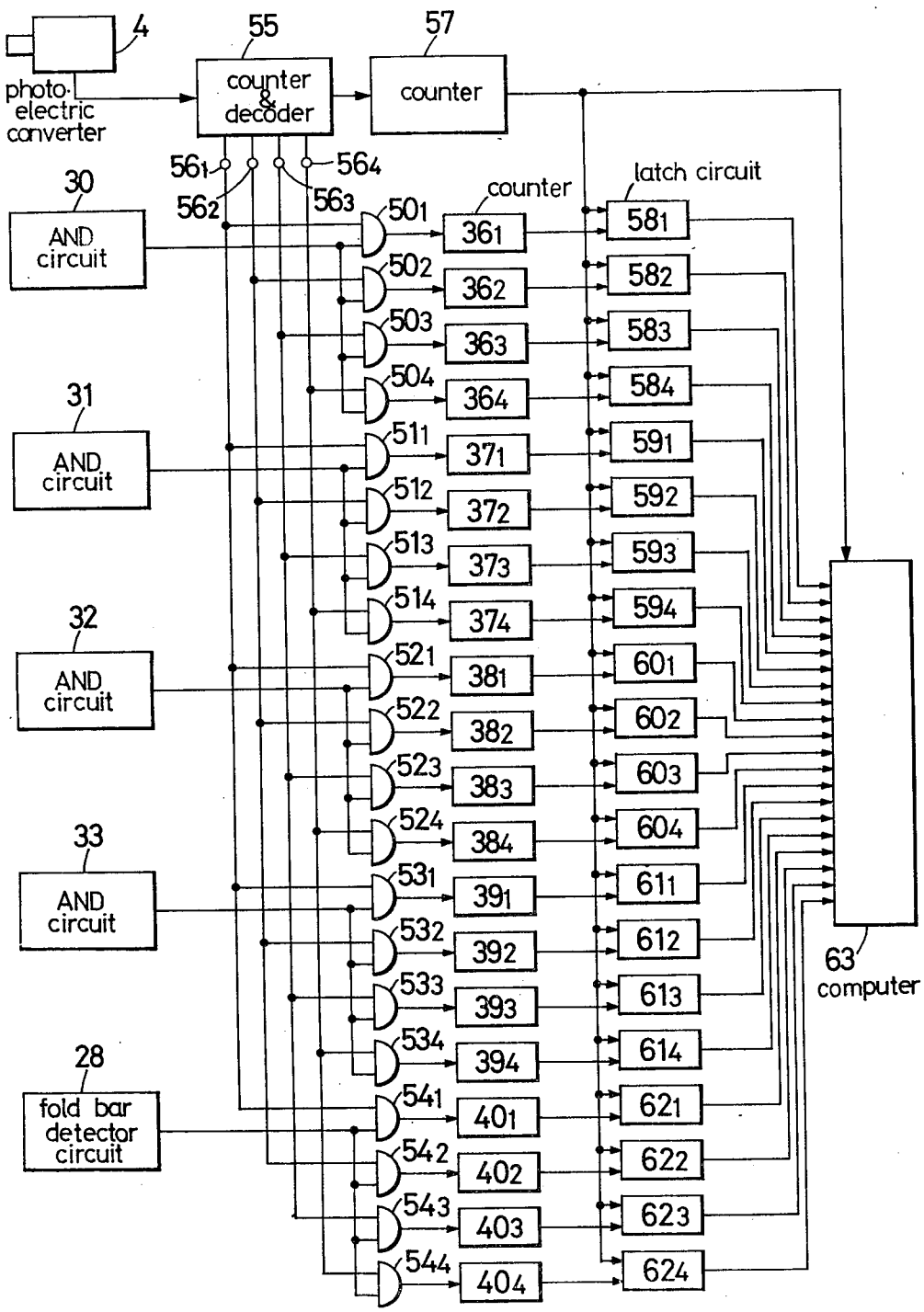
FIG. 6 is a block diagram illustrating one example of the construction for reading count values of respective defects in a processor.

In the manner described above, various drawbacks of the non-woven fabric are detected. The grading of the quality of the non-woven fabric is performed based on the drawbacks in the following manner. Namely, the non-woven fabric 1 is divided into unit areas $A_{11}$, $A_{12}$, $A_{13}$, $A_{14}$, $A_{21}$, $A_{22}$, $A_{23}$, $A_{24}$, ... $A_{n1}$, $A_{n2}$, $A_{n3}$ and $A_{n4}$ in a matrix form, as shown in FIG. 5. Each unit area is, for example, 10cm $\times$ 10cm and the area to be evaluated which is an assembly of the unit areas is selected to be 1m in the lengthwise direction of the non-woven fabric 1. The same number of counters as the kinds of the abovesaid drawbacks are provided respectively corresponding to the number of the unit areas in the widthwise direction of the non-woven fabric 1, which is four in this example. That is, as illustrated in FIG. 6, counters $36_1$ to $36_4$ for counting the number of holes are provided, which are supplied with the output from the AND circuit 30 of FIG. 4 through gates $50_1$ to $50_4$, respectively. In a likewise manner, the outputs from the AND circuits 31, 32 and 33 are respectively applied to heavy weight counters $37_1$ to $37_4$, light weight counters $38_1$ to $38_4$ and heavy filling bar counters $39_1$ to $39_4$ through gates $51_1$ to $51_4$, $52_1$ to $52_4$ and $53_1$ to $53_4$, respectively. And the output from the detector circuit 28 is applied to fold bar counters $40_1$ to $40_4$ through gates $54_1$ to $54_4$, respectively.

The photoelectric converter 4 derives therefrom a pulse having a width $\frac{1}{4}$ of its one scanning period. This pulse is applied to a 4-step counter and decoder 55, which produces an output at each of its terminals $56_1$ to $56_4$ one after another upon every counting of pulse. The width of each of the output pulses derived at the terminals $56_1$ to $56_4$ is selected to be $\frac{1}{4}$ of one scanning period. The outputs produced at the terminals $56_1$ and $56_2$ are respectively applied to the gates $50_1$, $51_1$, $52_1$, $53_1$, $54_1$ and $50_1$, $51_2$, $52_2$, $53_2$, $54_2$. Likewise, the outputs at the terminals $56_2$ and $56_4$ are respectively applied to the gates $50_3$, $51_3$, $52_3$, $53_3$, $54_3$ and $50_4$, $51_4$, $52_4$, $53_4$, $54_4$. Accordingly, for example, in FIG. 5, the uppermost part of the first unit area $A_{11}$ of the non-woven fabric 1 is scanned for detecting the drawbacks and, in this case, an output is produced at an output terminal $56_1$ and the gates $50_1$, $51_1$, $52_1$, $53_1$ and $54_1$ are opened and the drawbacks thus detected are individually counted by the counters $36_1$, $37_1$, $38_1$, $39_1$, $40_1$. When the scanning is shifted to the unit area $A_{12}$, the gates $50_2$, $51_2$, $52_2$, $53_2$ and $54_2$ are opened and the detected defects are individually counted by the counters $36_2$, $37_2$, $38_2$, $39_2$ and $40_2$. Such scanning is achieved for each of the unit areas. When the scanning is shifted to a second scanning line of the unit area $A_{11}$ due to travelling of the non-woven fabric 1, the defects detected in this case are respectively added to the count values already counted by the counters $36_1$, $37_1$, $38_1$, $39_1$ and $40_1$ for the previous scanning. In this manner, the lengths or numbers of the drawbacks of the respective unit areas are individually counted by the counters. Upon completion of scanning of the last scanning lines of the unit areas $A_{11}$ to $A_{15}$, 128-step counter 57, which is driven by a carry output from a counter 55, derives therefrom an output, by which the count values of the drawback counters $36_1$ to $36_4$, ... and $40_1$ to $40_4$ are latched in latch circuits $58_1$ to $58_4$, ... and $62_1$ to $62_4$ respectively corresponding thereto and these counters are reset and, in addition, an interruption request is applied to an electronic computer 63. Upon receipt of the interruption request, the electronic computer 63 reads in the contents latched in the latch circuits $58_1$ to $58_4$, ... and $62_1$ to $62_4$ one after another and stores them at addresses respectively predetermined for the unit areas. Similarly, the drawbacks of the unit areas $A_{12}$ to $A_{14}$ are counted and stored in the computer 63. Thus, the number of each drawbacks of each of the unit areas $A_{11}$ to $A_{14}$ is counted and stored.

Thereafter, in the computer 63, the count values stored therein are processed as follows. Namely, the count values are respectively read out and the respective unit areas are classified into a plurality of ranks in accordance with the numbers of the individual defects. For example, four ranks O, A, B and C are employed as depicted in FIG. 7, in which the ranks O, A, B and C respectively corresponds to the numbers of defects less than $\epsilon_1$, between $\epsilon_1$ and $\epsilon_2$, between $\epsilon_2$ and $\epsilon_3$ and more than $\epsilon_3$. Thus, each unit area is ranked in connection with each kind of drawback. Accordingly, each unit area is ranked O, A, B or C in connection with each of a hole defect $D_1$, a light weight defect $D_2$, heavy weight defect $D_3$, a heavy filling bar defect $D_4$ and a fold bar defect $D_5$. That is, the non-woven fabric is ranked according to the number of defects of each kind in each unit area.

Further, the ranks of each kind of defect in each evaluation area are counted. Thus, as shown in FIG. 8, the numbers $S_{10}$, $S_{11}$, ... and $S_{53}$ of the ranks O to C of the defects $D_1$ to $D_5$ in the evaluation area are obtained. Further, these total values $S_{10}$ to $S_{53}$ of the respective ranks are respectively compared with predetermined set values according to the ranks. Namely, as shown in FIG. 9A, the total value $S_{10}$ of the rank O of the hole defect $D_1$ is compared with set values $e_{01}$, $e_{02}$, $e_{03}$ and $e_{04}$ and the total value $S_{10}$ is classified as O when it is smaller than $e_{01}$, $W_0$ when it is between $e_{01}$ and $e_{02}$, $W_1$ when it is between $e_{02}$ and $e_{03}$, $W_2$ when it is between $e_{03}$ and $e_{04}$ and $W_3$ when it is larger than $e_{04}$. Likewise, the total value $S_{11}$ of the rank A of the defect $D_1$ is compared with set values $e_{11}$, $e_{12}$, $e_{13}$ and $e_{14}$ and the total value $S_{11}$ is classified as O when it is smaller than $e_{11}$, $W_0$ when it is between $e_{11}$ and $e_{12}$, $W_1$ when it is between $e_{12}$ and $e_{13}$, $W_2$ when it is between $e_{13}$ and $e_{14}$ and $W_3$ when it is larger than $e_{14}$, as shown in FIG. 9B. Similarly, the total value $S_{12}$ of the rank B of the defect $D_1$ is classified into O to $W_3$ as shown in FIG. 9C and the total value $S_{13}$ of the rank C of the defect $D_1$ is also classified into O to $W_3$ as depicted in FIG. 9D. Thus, the total values are respectively classified into the four classes O to C and the method of classification is as follows: for example, the total value $S_{10}$ is compared with each of the set values $e_{01}$, $e_{02}$, $e_{03}$ and $e_{04}$ and the largest one of the values exceeding these set values, for example, $e_{01}$ and $e_{02}$, is classified as $W_1$ corresponding to the set value $e_{02}$. Further, these set values are selected so that even if the total values of different ranks are equally classified as $W_1$, the set values of the higher rank are larger than those of the lower rank. Namely, where the total values of the ranks O and A of the same defect are equal to each other, the set values are selected so that $e_{01} > e_{11}$ and that $e_{02} > e_{12}$, ... because the rank A is indicative of lower quality.

Also in connection with the light weight defect $D_2$, the total values $S_{20}$ to $S_{23}$ of respective ranks are each classified into any of O to $W_3$. Similarly, the total values $S_{30}$ to $S_{33}$, $S_{40}$ to $S_{43}$ and $S_{50}$ to $S_{53}$ of the respective ranks of the heavy weight defect $D_3$, the heavy filling bar defect $D_4$ and the fold bar $D_5$ are also classified into O to $W_3$. As described above, the set values corresponding to the ranks of the same kind of defect are selected to decrease as the ranks lower. On the other hand, the corresponding set values among different kinds of defects bear the following relationships. That is, the hole defect $D_1$ is said to be fatal and regarded as a bad defect and the heavy filling bar $D_4$ is also regarded serious because it is extremely thick. The light weight $D_2$ and the heavy weight $D_3$ are that some particular areas are thin and thick as a whole, and their influence on the quality of the non-woven fabric is not so great as the hole and the heavy filling bar. Accordingly, the corresponding set values for the defects $D_1$ and $D_4$ are selected smaller than those for the defects $D_2$ and $D_3$. The streak defect $D_5$ presents a problem when many streaks exist and when the streak is small in number, it is unnoticeable, so that the corresponding set values are selected larger than those for the defects $D_1$ and $D_4$.

In the above manner, the total values of the respective ranks O to C of the defects $D_1$ to $D_5$ are classified into the four classes O to $W_3$. And the worst one of the values in each of these classes is used as the grading of the quality of the evaluation area. The grading may also be effected by synthesizing the generating conditions of the total values of the respective classes for the respective ranks of the defects.

Next, one experimental example of this invention will be described. Use was made of such a non-woven fabric 1 as shown in FIG. 10, which was a white nylon sheet 1m wide, 1m long and 60g/m² thick. The right-hand evaluation area had a hole 64, a heavy weight area 65 adjacent to the hole 64, a heavy filling bar area 66 in the heavy weight area 65 and a wide light weight area 67 and the left evaluation area had a fold bar area 68. Two photoelectric converters were employed for respectively scanning the left- and right-hand evaluation areas, each 50×100cm. The travelling speed of the non-woven fabric was 30m/min.; the scanning speed of each photoelectric converter was 2μS/line; a minimum detection capacity of the photoelectric converter was 0.5mm wide × 1mm long; the number of photoelectric conversion elements of the converter was 1024; and a scanning clock frequency was 7500 KHz. And a 80W DC-lighting fluorescent lamp 110cm long was disposed as a light source across the non-woven fabric 1.

The output from the envelope detector circuit 20 on a scanning line 69 contained a negative pulse 71 corresponding to the fold bar area 68, a high level 72 corresponding to the hole 64 and a thin portion 73 corresponding to the heavy weight area 65, as shown in FIG. 11a. The output from the envelope detector circuit 20 corresponding to a scanning line 74 contained a portion 75 of relatively high level corresponding to the light weight area. Each unit area was 12.5cm × 12.5cm, the scanning lines of each unit area was 128 and the scanning points of one scanning line of each unit area were 256. The count values of the "hole" counter in connection with the respective unit areas are shown in FIG. 12A corresponding to the unit areas. The count values in the unit areas of the left-hand evaluation area are all zero, which indicates that no hole is formed in the left-hand evaluation area. The count value in the unit area $A_{13}$ of the right-hand evaluation area is 485 and the count value in the unit area $A_{14}$ is 23 since the hole 64 a little extends into this unit area. Similarly, the count values of the counter for the light weight are shown in FIG. 12B and the count values of the counters for the heavy weight, the heavy filling bar and the fold bar are respectively shown in FIGS. 12C, 12D and 12E. Since the light and heavy weights are counted by detecting small level variations, they are large in number but the number of about 1000 is very small as compared with the total number of bits of each unit area, that is, the number of scanning points therein. For the ranking described previously with regard to FIG. 7, the numbers $\epsilon_1$, $\epsilon_2$ and $\epsilon_3$ of the defects $D_1$ to $D_5$ are shown in FIG. 13. For example, in the case of the hole defect $D_1$, each unit area is ranked as O, A, B or C depending upon whether the number of defects of this kind in the unit area is less than 2, between 2 to 60, between 60 to 500 or more than 500. Accordingly, in FIG. 12A, the unit area $A_{12}$ of the right-hand evaluation area is ranked as B because it contains 485 hole defects and the unit area $A_{13}$ is ranked as A because it contains 23 hole defects. The unit areas $A_{21}$, $A_{22}$ and $A_{23}$ are all ranked as B and the unit areas $A_{31}$, $A_{32}$ and $A_{33}$ are all ranked C because they have more than 580 hole defects. Thus, in connection with each defect, the count value of each unit area is ranked as any one of O, A, B and C. Then, the numbers of the ranks O to C for the respective defects are individually added together and the total values are compared with set values for classification as shown in FIG. 9. To this end, the set values were selected as depicted in FIG. 14. For example, in connection with the total values of the rank B of the hole defect $D_1$, they are respectively classified as $W_2$ and $W_3$ when they are in the range of 1 to 32 and more than 32. And only the worst class of each defect is provided as an output. The results of such classification are shown in FIGS. 15A and 15B in connection with the right- and left-hand evaluation areas, respectively. In the left-hand evaluation area, the defects $D_1$ to $D_4$ are all classified normal but only the fold bar defect $D_5$ is classified as $W_0$ due to the presence of the fold bar area 68. In the right-hand evaluation area, the hole defect $D_1$ is classified as the worst class $W_3$. The fold bar defect $D_5$ is classified as $W_1$ and this is because the portion corresponding to the margin of the hole 64 appears in the output from the differentiation circuit 27 (FIG. 1).

In the above, images at the respective points on the non-woven fabric in its widthwise direction were focused by a camera onto the array of photodiodes and converted by switching into electric signals. However, it is also possible to employ such a method in which the non-woven fabric is scanned by a laser beam in its widthwise direction and the transmitted light is converted by one photoelectric conversion element into an electric signal. Further, it is also possible to pick up the image of the non-woven fabric with a TV camera and to repeatedly scan only one scanning line. In this case, there is no need of switching and a continuous output can be obtained as in the case of employing the laser beam. Moreover, in the foregoing, light transmitted through the non-woven fabric is utilized but a reflected light can be used. Further, in the above, the portion corresponding to the hole is counted as a light weight, too, but it is also possible to subtract the count value of the hole from the count value of the light weight or since the hole defect is remarkedly important, its count value may be greatly weighted and processed without such a subtraction and this does not greatly affect the quality.

In the conventional method of detection of defects of the non-woven fabric, various studies have been made only for facilitating visual inspection of the non-woven fabric. With this invention, however, various defects can be automatically detected and, by differentiation processing, the output corresponding to the fold bar can be easily obtained. This differentiated output is produced also in the case of the hole defect and the heavy filling bar defect and this increases a little the number of fold bars as described above. However, the fold bar is not so important as a whole and presents a problem only when its number is large, so that the number of fold bars is essentially detected even if not detected accurately. Accordingly, automatic detection can be achieved by simple processing. This automatic detection of the defects allows ease in the grading of the quality of the non-woven fabric, too, and eliminates the necessity of unwinding of manufactured articles for inspection and enables classifying of the manufactured articles according to their quality immediately after they are manufactured.

It will be apparent that many modifications and variations may be effected without departing from the scope of the novel concepts of this invention.

What is claimed is:

1. A non-woven fabric defect detecting device, comprising:
   a light source for irradiating a travelling non-woven fabric by light;
   a photoelectric converter for receiving a transmitted light or reflected light from the non-woven fabric and converting it into an electric signal output;
   scanning means for sequentially picking up the converted output corresponding to each point on the non-woven fabric in its widthwise direction;
   means for classifying the converted output into a plurality of levels and individually detecting a plurality of kinds of defects;
   a differentiation circuit for differentiating the converted output;
   a fold bar detector circuit for detecting a differentiated output exceeding a predetermined level;
   and characterized by:
   a mean level detector circuit for detecting the mean level of the converted output from the converter; and
   circuit means for controlling the light source in accordance with the detected level so that the mean level of the converted output applied to the classifying and defect detecting means is maintained constant.

2. The device according to claim 1, wherein said classifying and defect detecting means comprises a hole detector circuit having a reference level for comparison with the converted output to detect a converted output level corresponding to a hole in the nonwoven fabric, and a heavy filling bar detector circuit having a reference level for comparison with the converted output to detect a converted output level corresponding to a heavy filling bar in the non-woven fabric.

3. The device according to claim 2, wherein the classifying and defect detecting means further comprises a light weight detector circuit having a reference level for comparison with the converted output to detect a converted output level corresponding to a light weight of the non-woven fabric, and a heavy weight detector circuit having a reference level for comparison with the converted output to detect a converted output level corresponding to a heavy weight of the non-woven fabric.

4. The device according to claim 1, wherein the classifying defect detecting means comprises a large bar detector circuit for detecting a large bar, a small bar detector circuit for detecting a small bar, a first amplifier for amplifying the converted output applied to the large bar detector circuit and a second amplifier having a gain larger than that of the first amplifier for amplifying the converted output applied to the small bar detector circuit.

5. The device according to claim 1, wherein the light source is a light source applying a uniform light to the non-woven fabric over a predetermined scanning area, and the photoelectric converter is a line scanning camera also serving as the scanning means, the line scanning camera comprising an array of photoelectric converting elements, the predetermined area of the non-woven fabric being focused into image and the outputs of the photoelectric converting elements being taken out by switching one after another.

6. The device according to claim 5, which further includes an envelope detector circuit for detecting the envelope of the output from the photoelectric converter and applying the detected envelope to the classifying and defect detecting means and to the differentiation circuit.

7. The device according to claim 1, which further includes counters for individually counting the durations of the defects detected by the classifying and defect detecting means and a counter for counting the number of the defects detected by the fold bar detector circuit.

8. The device according to claim 7 which further includes means for individually obtaining the total values of the defects of each unit area of the non-woven fabric counted by the counters and defect adding for classifying the count values into a plurality of ranks and individually adding together the numbers of the ranks of the respective defects in an evaluation area formed by an assembly of the unit areas.

* * * * *